(12) United States Patent
Su et al.

(10) Patent No.: US 10,493,054 B2
(45) Date of Patent: *Dec. 3, 2019

(54) DOCETAXEL ALBUMIN NANOPARTICLE PHARMACEUTICAL COMPOSITION, PREPARATION METHOD THEREFOR AND USE THEREOF

(71) Applicant: SICHUAN KELUN PHARMACEUTICAL RESEARCH INSTITUTE CO. LTD., Chengdu, Sichuan (CN)

(72) Inventors: Zhengxing Su, Sichuan (CN); Likai Yang, Sichuan (CN); Dong Zhao, Sichuan (CN); Jing Zhou, Sichuan (CN); Fengying Shan, Sichuan (CN); Lichun Wang, Sichuan (CN); Jingyi Wang, Sichuan (CN)

(73) Assignee: SICHUAN KELUN PHARMACEUTICAL RESEARCH INSTITUTE CO. LTD., Chengdu, Sichuan (CN)

( * ) Notice: Subject to any disclaimer, the term of this patent is extended or adjusted under 35 U.S.C. 154(b) by 29 days.

This patent is subject to a terminal disclaimer.

(21) Appl. No.: 15/548,443

(22) PCT Filed: Mar. 28, 2016

(86) PCT No.: PCT/CN2016/077521
§ 371 (c)(1),
(2) Date: Aug. 3, 2017

(87) PCT Pub. No.: WO2016/155595
PCT Pub. Date: Oct. 6, 2016

(65) Prior Publication Data
US 2018/0028486 A1    Feb. 1, 2018

(30) Foreign Application Priority Data
Apr. 3, 2015 (CN) .......................... 2015 1 0157393

(51) Int. Cl.
| | | |
|---|---|---|
| A61K 31/337 | (2006.01) | |
| A61K 47/42 | (2017.01) | |
| A61K 9/14 | (2006.01) | |
| A61K 47/16 | (2006.01) | |

(Continued)

(52) U.S. Cl.
CPC .............. *A61K 31/337* (2013.01); *A61K 9/14* (2013.01); *A61K 9/5192* (2013.01); *A61K 47/16* (2013.01); *A61K 47/18* (2013.01); *A61K 47/42* (2013.01)

(58) Field of Classification Search
None
See application file for complete search history.

(56) References Cited

FOREIGN PATENT DOCUMENTS

| CN | 101361731 | * | 8/2008 |
| CN | 101658516 | * | 8/2008 |

(Continued)

OTHER PUBLICATIONS

Translation of CN 101658516 downloaded Feb. 11, 2019 from https://patents.google.com/patent/CN101658516A/en?oq=101658516 (Year: 2008).*

(Continued)

*Primary Examiner* — Karl J Puttlitz
(74) *Attorney, Agent, or Firm* — Rothwell, Figg, Ernst & Manbeck, P.C.

(57) ABSTRACT

The present invention relates to a docetaxel albumin nanoparticle pharmaceutical composition, a preparation method therefor, and a use thereof for manufacturing drugs for treating cancer. The pharmaceutical composition comprises docetaxel, albumin and amino acid(s), wherein the weight ratio between albumin and docetaxel is no more than 50, preferably is 20:1 to 1:1, and the weight ratio between amino acid(s) and docetaxel is not less than 0.5, preferably is 1:1 to 20:1.

22 Claims, 1 Drawing Sheet

(51) Int. Cl.
    *A61K 9/51*    (2006.01)
    *A61K 47/18*   (2017.01)

(56) References Cited

FOREIGN PATENT DOCUMENTS

| | | |
|---|---|---|
| CN | 101361731 A | 2/2009 |
| CN | 101658516 A | 3/2010 |
| CN | 101972480 A | 2/2011 |
| CN | 103202813 A | 7/2013 |
| CN | 103751107 A | 4/2014 |
| WO | 2007027941 A2 | 3/2007 |
| WO | 2011088688 A1 | 7/2011 |

OTHER PUBLICATIONS

Translation of CN 101361731 downloaded Feb. 11, 2019 from https://patents.google.com/patent/CN101361731A/en?oq=101361731 (Year: 2008).*
Machine Translation of CN 101804021, downloaded Aug. 27 from https://patents.google.com/patent/CN101804021B/en?oq=CN+101804021 (Year: 2010).*
Eurasian Office Action with English Translation issued in Application No. 201791537 dated Jul. 25, 2018, 8 pages.
First Chinese Office Action with English translation, issued in Chinese Application No. 201510157393.1, dated May 3, 2018, 15 pages.
The extended European Search Report issued in Application No. 16771350.2 dated Nov. 6, 2018, 7 pages.
International Search Report dated Jun. 15, 2016 issued in PCT/CN2016/077521.

* cited by examiner

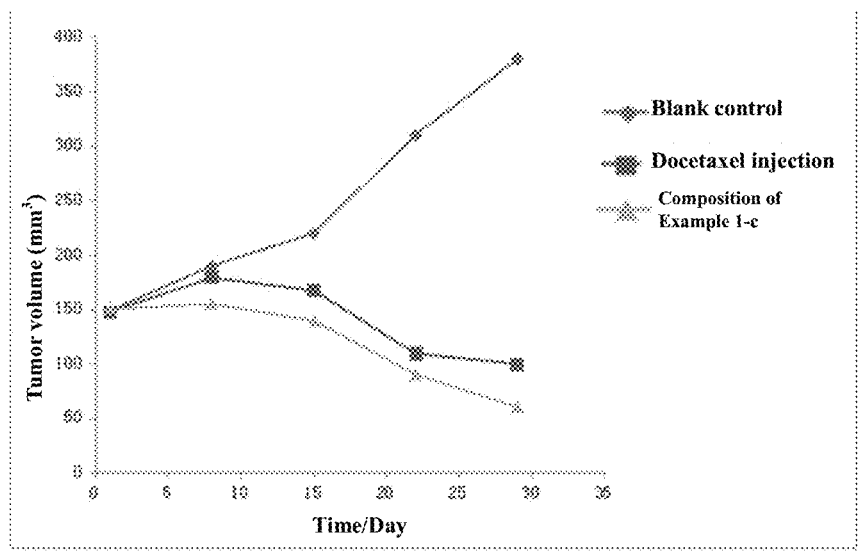

2

DOCETAXEL ALBUMIN NANOPARTICLE PHARMACEUTICAL COMPOSITION, PREPARATION METHOD THEREFOR AND USE THEREOF

CROSS-REFERENCE TO RELATED APPLICATIONS

The present application is a national stage filing under 35 U.S.C. § 371 of PCT/CN2016/077521, filed on 28 Mar. 2016, and claims priority to Chinese patent application 201510157393.1, filed 3 Apr. 2015. Each application is incorporated herein by reference in its entirety.

FIELD OF THE INVENTION

The present invention pertains to the field of pharmaceutical compositions of docetaxel (docetaxol), specifically relates to a docetaxel albumin nanoparticle pharmaceutical composition, preparation method therefor and use thereof, and especially relates to a docetaxel albumin nanoparticle pharmaceutical composition with improved stability, preparation method therefor and use thereof.

BACKGROUND OF THE INVENTION

Docetaxel belongs to taxane drugs. The main mechanism of action thereof involves interfering with mitosis, promoting the assembly of microtubules and prohibiting the disassembly of microtubules, so as to inhibit the differentiation of tumor cells, and finally lead to death thereof. Currently, docetaxel is approved for the treatment of various indications such as breast cancer, non-small cell lung cancer, prostate cancer and the like in major countries worldwide, and it constitutes the most commonly used or standard therapy for the treatment of these cancers. Furthermore, in subsequent clinical studies, docetaxel is also widely investigated for the treatment of gastric cancer, head and neck tumor, esophageal cancer, ovarian cancer, and the like. Treatment of these indications with docetaxel is expected to be approved in Europe and America later.

Docetaxel has poor water solubility. Presently, the formulation of docetaxel commercially available is a liquid dosage form for infusion in a concentrated form, and the dosage regimen normally recommended is intravenous infusion of 75 mg/m² within 1 hour, once every 3 weeks. A docetaxel injection comprises a drug concentrate, which is formed by dissolving docetaxel in a solvent, Tween-80, accompanied with a diluent containing 13% ethanol. However, pre-application of an anti-allergic drug is necessary during clinical administration due to the hemolytic property of Tween-80, which tends to cause allergic reactions including dyspnea, hypotension, angioedema, rubella, shock, etc. when it is intravenously injected. Moreover, the high viscosity of Tween-80 also brings about great inconvenience in clinical application.

In order to overcome defects of the docetaxel injection, such as toxic side effects and the like, CN103830181A discloses a lyophilized liposome comprising an inclusion complex of docetaxel with cyclodextrin, wherein the stability of docetaxel is improved by inclusion with cyclodextrin, and an improved targeting property and reduced toxic side effects are achieved with the liposome particle system. However, the toxicity of cyclodextrin per se limits the application thereof. CN101773465A discloses a polymeric micellar system stabilized by amino acids, and a polymeric micelle comprising docetaxel is developed. It is shown that the physical appearance of the polymeric micelle with amino acids can be stable for more than 5 days, while the polymeric micelle without amino acids can be stable only for 30 minutes. However, the degradation of high molecular polymers (e.g., mPEG-PLA, etc.) employed in polymeric micelles after being injected into a body is quite slow, and may even last for more than 1 year. In view of such potential safety issues, no polymeric micelle product of docetaxel has been approved for marketing by the FDA in the United States. As such, although improved targeting properties and reduced toxic side effects are achieved with these particle systems, the application thereof is limited by their defects.

CN103054798A discloses a docetaxel albumin nanoparticle (ABI-008), wherein citric acid (or a salt thereof) is added to a composition of docetaxel and albumin, such that the physical stability of a solution of the docetaxel albumin nanoparticle is increased, and no precipitation or sedimentation phenomenon is observed for at least 8 hours after reconstitution or rehydration.

However, for improving the stability of docetaxel, in addition to control the physical stability of particles in a solution, it is more important to reduce the chemical degradation of docetaxel. At present, studies focusing on reducing the chemical degradation of docetaxel are quite limited in the prior art, and no method for improving such degradation is available yet.

Docetaxel per se can undergo a variety of degradation pathways under various conditions, and degradation products resulted therefrom render corresponding changes in the activity and/or toxicity of docetaxel, and may even significantly affect the activity and/or toxicity thereof. The main factors affecting the degradation of docetaxel include temperature, acidic and basic solvents, oxidants, reductants and light, etc.

In a basic, neutral or strong acidic medium, one of the main degradation pathways of docetaxel is the epimerization of 7-hydroxy, which results in 7-epi-docetaxel through retro-aldol reaction.

Bornique et al. (Drug Metabolism and Disposition, Vol. 30, No. 11, pp. 1149-1152, 2002) investigates the interaction between docetaxel and 7-epi-docetaxel with recombinant human cytochrome P4501B1 (hCYP1B1). hCYP1B1 is a common cytochrome in human tumor cells, and is mainly related to drug resistance of chemotherapy drugs (including docetaxel). The in vitro test shows that the activity of hCYP1B1 can be increased by more than 7 times by 7-epi-docetaxel, thus it is confirmed that the degradation product of docetaxel, 7-epi-docetaxel, reduces the activity of docetaxel.

CN101415416A discloses inhibition of the production of 7-epi-docetaxel in a pharmaceutical composition of docetaxel and polysorbate 80 by adding an organic acid with a pKa value of 2.5 to 4.5 as a docetaxel degradation inhibitor.

However, the inventors of the present invention have demonstrated through experimentation that addition of an agent such as tartaric acid, citric acid, ascorbic acid or another organic acid with a pKa value of 2.5 to 4.5 etc. into a composition of docetaxel and albumin cannot effectively inhibit the production of 7-epi-docetaxel, which, instead, may even increase. This indicates that the above agents decrease the chemical stability of the composition, and affect the safety of the final formulation.

CN103054798A discloses addition of a stabilizer such as citric acid (or a salt thereof) and the like into a composition of docetaxel and albumin. Although the stabilizer enhances the physical stability of the solution of the docetaxel albumin nanoparticle, the inhibitory effect thereof on the production of 7-epi-docetaxel is not mentioned.

It has been demonstrated through experimentation that conventional stabilizers such as citric acid (or a salt thereof) and the like cannot always effectively inhibit the production of 7-epi-docetaxel, and sometimes the production thereof may be accelerated. During storage, the amount of 7-epi-docetaxel produced far exceeds 2.0%, which would results in potential safety issues in clinical medication.

One of the challenges in search for a method for inhibiting the production of 7-epi-docetaxel is that, during the storage of a docetaxel albumin nanoparticle, the presence of a large amount of hydrogen bonds in the polypeptidic structure of albumin is unfavorable for the stability of docetaxel and accelerates the retro-aldol reaction, which result in the epimerization of 7-hydroxyl, rendering the formation and steady increase of the 7-epi-docetaxel impurity.

As such, it is an urgent problem to be solved in the art to find a method for inhibiting the production of 7-epi-docetaxel in a pharmaceutical composition of docetaxel.

SUMMARY OF THE INVENTION

In view of the defects in the prior art, according to an aspect of the present invention, a docetaxel albumin nanoparticle pharmaceutical composition with enhanced stability is provided, wherein the pharmaceutical composition comprises:
  docetaxel,
  albumin, and
  amino acid(s),
wherein the weight ratio of albumin to docetaxel is not greater than 50, i.e., is from 50:1 to >0:1, preferably is from 50:1 to 1:1, and more preferably is from 20:1 to 1:1.

According to another aspect of the present invention, the above docetaxel albumin nanoparticle pharmaceutical composition is provided, wherein the weight ratio of the amino acid(s) to docetaxel is no less than 0.5, i.e., is ≥0.5:1, preferably is from 0.5:1 to 80:1, more preferably is no less than 1, i.e., is ≥1:1, and preferably is from 1:1 to 20:1.

According to another aspect of the present invention, the above docetaxel albumin nanoparticle pharmaceutical composition is provided, wherein the pharmaceutical composition further comprises a protein structure unfolding agent.

According to another aspect of the present invention, a method for preparing the above docetaxel albumin nanoparticle pharmaceutical composition is provided.

According to another aspect of the present invention, a formulation comprising the above docetaxel albumin nanoparticle pharmaceutical composition is provided, and the formulation further comprises a pharmaceutically acceptable carrier and/or auxiliary material.

According to another aspect of the present invention, a use of the above pharmaceutical composition or the above formulation in the manufacture of a medicament for the treatment of cancer is provided.

According to another aspect of the present invention, a method for treating cancer is provided, wherein the method comprises administering to a subject in need thereof an effective amount of the above pharmaceutical composition or the above formulation.

According to another aspect of the present invention, the above pharmaceutical composition or the above formulation for the treatment of cancer is provided.

Surprisingly, it is found that the addition of amino acid(s) can result in a docetaxel albumin nanoparticle pharmaceutical composition which is stable for a long time, and can significantly inhibit the production of 7-epi-docetaxel in the pharmaceutical composition. According to an embodiment of the present invention, addition of amino acid(s) into a docetaxel albumin nanoparticle pharmaceutical composition can result in a composition with a content of 7-epi-docetaxel below 1% after being stored for 24 months (e.g. at 2-8° C.). Particularly, when the amino acid employed is arginine, the content of 7-epi-docetaxel is preferably below 1%, such as about 0.98%, about 0.83%, about 0.75%, about 0.72% or even lower, after 30 months of storage (e.g. at 2-8° C.).

BRIEF DESCRIPTION OF THE DRAWING

FIG. 1 shows the pharmacological efficacy results of the composition of Example 1-c in the treatment of a subcutaneous xenograft of human non-small cell lung cancer cell A549 in a tumor model of BALB/c nude mice.

DETAILED DESCRIPTION OF THE INVENTION

Pharmaceutical Composition and Preparation Method Therefor

An embodiment of the present invention provides a docetaxel albumin nanoparticle pharmaceutical composition, wherein the pharmaceutical composition comprises:
  docetaxel,
  albumin, and
  amino acid(s),
wherein the weight ratio of albumin to docetaxel is not greater than 50, i.e., is from 50:1 to >0:1, preferably is from 50:1 to 1:1, and more preferably is from 20:1 to 1:1.

A further embodiment of the present invention provides the above docetaxel albumin nanoparticle pharmaceutical composition, wherein the weight ratio of the amino acid(s) to docetaxel is no less than 0.5, i.e., is ≥0.5:1, preferably is from 0.5:1 to 80:1, more preferably is no less than 1, i.e., is ≥1:1, and preferably is from 1:1 to 20:1.

A further embodiment of the present invention provides the above docetaxel albumin nanoparticle pharmaceutical composition, which further comprises a protein structure unfolding agent including, e.g., one or more of mercaptoethanol, glutathione, acetylcysteine, and dithiothreitol, wherein the weight ratio of albumin to the protein structure unfolding agent is not greater than 100:1, i.e., is from 100:1 to >0:1, such as from 90:1 to >0:1, from 80:1 to >0:1, from 70:1 to >0:1, from 60:1 to >0:1, from 50:1 to >0:1, from 40:1 to >0:1, from 30:1 to >0:1, from 20:1 to >0:1 or from 10:1 to >0:1, and preferably is from 50:1 to >0:1.

A further embodiment of the present invention provides the above docetaxel albumin nanoparticle pharmaceutical composition, wherein the pharmaceutical composition is a nanoparticle suspension, which comprises docetaxel in a concentration of at least 1 mg/ml, and the nanoparticles therein have a particle diameter of not greater than 200 nm.

Another embodiment of the present invention provides a method for preparing the above docetaxel albumin nanoparticle pharmaceutical composition, wherein the method comprises the following steps:

1) dissolving docetaxel in an organic solvent preferably selected from one or more of ethanol, tert-butyl alcohol, and acetone, to obtain an organic phase;

2) using an aqueous solution containing amino acid(s) to dissolve albumin or to dilute a solution of albumin, so as to obtain a solution of albumin and amino acid(s);

3) adding a protein structure unfolding agent to the solution of albumin and amino acid(s) obtained in step 2), and performing an incubation reaction; wherein the protein structure unfolding agent includes one or more of mercaptoethanol, glutathione, acetylcysteine, and dithiothreitol;

4) adding the organic phase obtained in step 1) to the solution obtained after the incubation reaction in step 3) under shear, to obtain a dilute solution of docetaxel albumin nanoparticles; and 5) concentrating the solution obtained in step 4) by ultrafiltration, to obtain a docetaxel albumin nanoparticle pharmaceutical composition with enhanced stability;

wherein the weight ratio of albumin to docetaxel is not greater than 50, i.e., is from 50:1 to >0:1, preferably is from 50:1 to 1:1, and more preferably is from 20:1 to 1:1; the weight ratio of the amino acid(s) to docetaxel is no less than 0.5, i.e., is ≥0.5:1, preferably is from 0.5:1 to 80:1, more preferably is no less than 1, i.e., is ≥1:1, and preferably is from 1:1 to 20:1; and the weight ratio of albumin to the protein structure unfolding agent is not greater than 100:1, i.e., is from 100:1 to >0:1, and preferably is from 50:1 to >0:1.

Another embodiment of the present invention provides a method for preparing the above docetaxel albumin nanoparticle pharmaceutical composition, wherein the method comprises the following steps:

1) dissolving docetaxel in an organic solvent preferably selected from one or more of ethanol, tert-butyl alcohol, and acetone, to obtain an organic phase;

2) using an aqueous solution containing amino acid(s) to dissolve albumin or to dilute a solution of albumin, so as to obtain a solution of albumin and amino acid(s);

3) subjecting the solution of albumin and amino acid(s) obtained in step 2) to an incubation reaction;

4) adding the organic phase obtained in step 1) to the solution obtained after the incubation reaction in step 3) under shear, to obtain a dilute solution of docetaxel albumin nanoparticles; and 5) concentrating the solution obtained in step 4) by ultrafiltration, to obtain a docetaxel albumin nanoparticle pharmaceutical composition with enhanced stability;

wherein the weight ratio of albumin to docetaxel is not greater than 50, i.e., is from 50:1 to >0:1, preferably is from 50:1 to 1:1, and more preferably is from 20:1 to 1:1; and the weight ratio of the amino acid(s) to docetaxel is no less than 0.5, i.e., is ≥0.5:1, preferably is from 0.5:1 to 80:1, more preferably is no less than 1, i.e., is ≥1:1, and preferably is from 1:1 to 20:1.

Another embodiment of the present invention provides a method for preparing the above docetaxel albumin nanoparticle pharmaceutical composition, wherein the method comprises the following steps:

1) dissolving docetaxel in an organic solvent preferably selected from one or more of ethanol, tert-butyl alcohol, and acetone, to obtain an organic phase;

2) using water for injection to dissolve albumin or to dilute a solution of albumin, so as to obtain a solution of albumin;

3) adding a protein structure unfolding agent to the solution of albumin obtained in step 2), and performing an incubation reaction; wherein the protein structure unfolding agent includes one or more of mercaptoethanol, glutathione, acetylcysteine, and dithiothreitol;

4) adding the organic phase obtained in step 1) to the solution obtained after the incubation reaction in step 3) under shear, to obtain a dilute solution of docetaxel albumin nanoparticles; and 5) concentrating the solution obtained in step 4) by ultrafiltration, adding amino acid(s) to the concentrate, wherein the weight ratio of the amino acid(s) to docetaxel is no less than 0.5, i.e., is ≥0.5:1, preferably is from 0.5:1 to 80:1, more preferably is no less than 1, i.e., is ≥1:1, and preferably is from 1:1 to 20:1, to obtain a docetaxel albumin nanoparticle pharmaceutical composition with enhanced stability;

wherein the weight ratio of albumin to docetaxel is not greater than 50, i.e., is from 50:1 to >0:1, preferably is from 50:1 to 1:1, and more preferably is from 20:1 to 1:1; and the weight ratio of albumin to the protein structure unfolding agent is not greater than 100:1, i.e., is from 100:1 to >0:1, and preferably is from 50:1 to >0:1.

Another embodiment of the present invention provides a method for preparing the above docetaxel albumin nanoparticle pharmaceutical composition, wherein the method comprises the following steps:

1) dissolving docetaxel in an organic solvent preferably selected from one or more of ethanol, tert-butyl alcohol, and acetone, to obtain an organic phase;

2) using water for injection to dissolve albumin or to dilute a solution of albumin, so as to obtain a solution of albumin;

3) subjecting the solution of albumin obtained in step 2) to an incubation reaction;

4) adding the organic phase obtained in step 1) to the solution obtained after the incubation reaction in step 3) under shear, to obtain a dilute solution of docetaxel albumin nanoparticles; and 5) concentrating the solution obtained in step 4) by ultrafiltration, adding amino acid(s) to the concentrate, wherein the weight ratio of the amino acid(s) to docetaxel is no less than 0.5, i.e., is ≥0.5:1, preferably is from 0.5:1 to 80:1, more preferably is no less than 1, i.e., is ≥1:1, and preferably is from 1:1 to 20:1, to obtain a docetaxel albumin nanoparticle pharmaceutical composition with enhanced stability;

wherein the weight ratio of albumin to docetaxel is not greater than 50, i.e., is from 50:1 to >0:1, preferably is from 50:1 to 1:1, and more preferably is from 20:1 to 1:1.

Another embodiment of the present invention provides a method for preparing the above docetaxel albumin nanoparticle pharmaceutical composition, wherein the method comprises the following steps:

1) dissolving docetaxel in an organic solvent preferably selected from one or more of ethanol, tert-butyl alcohol, and acetone, to obtain an organic phase;

2) using water for injection to dissolve albumin or to dilute a solution of albumin, so as to obtain a solution of albumin;

3) adding amino acid(s) and a protein structure unfolding agent to the solution of albumin obtained in step 2), and performing an incubation reaction; wherein the protein structure unfolding agent includes one or more of mercaptoethanol, glutathione, acetylcysteine, and dithiothreitol;

4) adding the organic phase obtained in step 1) to the solution obtained after the incubation reaction in step 3) under shear, to obtain a dilute solution of docetaxel albumin nanoparticles; and 5) concentrating the solution obtained in step 4) by ultrafiltration, to obtain a docetaxel albumin nanoparticle pharmaceutical composition with enhanced stability;

wherein the weight ratio of albumin to docetaxel is not greater than 50, i.e., is from 50:1 to >0:1, preferably is from 50:1 to 1:1, and more preferably is from 20:1 to 1:1; the weight ratio of the amino acid(s) to docetaxel is no less than 0.5, i.e., is ≥0.5:1, preferably is from 0.5:1 to 80:1, more preferably is no less than 1, i.e., is ≥1:1, and preferably is from 1:1 to 20:1; and the weight ratio of albumin to the protein structure unfolding agent is not greater than 100:1, i.e., is from 100:1 to >0:1, and preferably is from 50:1 to >0:1.

Another embodiment of the present invention provides a method for preparing the above docetaxel albumin nanoparticle pharmaceutical composition, wherein the method comprises the following steps:

1) dissolving docetaxel in an organic solvent preferably selected from one or more of ethanol, tert-butyl alcohol, and acetone, to obtain an organic phase;
2) using water for injection to dissolve albumin or to dilute a solution of albumin, so as to obtain a solution of albumin, and then adding amino acid(s);
3) subjecting the solution of albumin obtained in step 2) to an incubation reaction;
4) adding the organic phase obtained in step 1) to the solution obtained after the incubation reaction in step 3) under shear, to obtain a dilute solution of docetaxel albumin nanoparticles; and
5) concentrating the solution obtained in step 4) by ultrafiltration, to obtain a docetaxel albumin nanoparticle pharmaceutical composition with enhanced stability;

wherein the weight ratio of albumin to docetaxel is not greater than 50, i.e., is from 50:1 to >0:1, preferably is from 50:1 to 1:1, and more preferably is from 20:1 to 1:1; and the weight ratio of the amino acid(s) to docetaxel is no less than 0.5, i.e., is ≥0.5:1, preferably is from 0.5:1 to 80:1, more preferably is no less than 1, i.e., is ≥1:1, and preferably is from 1:1 to 20:1.

According to the above embodiments, amino acid(s) can be added before or after the formation of nanoparticles during the preparation of the docetaxel albumin nanoparticle pharmaceutical composition of the present invention. During the preparation of the present composition, any method can achieve the effect of the present invention, as long as it can mix docetaxel albumin nanoparticles with amino acid(s). The above-listed methods are merely major ones, and without departing from the spirit of the present invention, other methods obtained through reasonable modifications to the above methods are covered by the present invention.

Unless otherwise defined in the context, all technical and scientific terms used herein are intended to have the same meaning as commonly understood by a person skilled in the art. References to techniques employed herein are intended to refer to the techniques as commonly understood in the art, including variations on those techniques or substitutions of equivalent techniques which would be apparent to a person skilled in the art. While it is believed that most of the following terms will be readily understood by a person skilled in the art, the following definitions are put forth to better illustrate the present invention.

The terms "contain", "include", "comprise", "have", or "involve", as well as other variations thereof used herein are inclusive or open-ended, and do not exclude additional, unrecited elements or method steps.

As used herein, the term "docetaxel" is also referred to as "Taxotere" or "docetaxel" in the art, and the "docetaxel" referred to in the present application comprises the docetaxel compound per se and derivatives or analogues thereof. The derivatives or analogues of docetaxel include but are not limited to compounds similar to docetaxel in structure, or compounds which belong to a same generic chemical species as that of docetaxel, such as taxanes. In some embodiments, the derivatives or analogues of docetaxel possess biological, pharmacological, chemical and/or physical properties (including, e.g., functionality) similar to those of docetaxel. Examples of the derivatives or analogues of docetaxel include paclitaxel and cabazitaxel. Moreover, as used herein, the term "docetaxel" also includes crystalline and amorphous forms, as well as anhydrite, hydrated forms (such as hemihydrate, dihydrate, trihydrate, and the like) and solvated forms (such as alcoholate) thereof.

As used herein, the term "albumin" includes one or more of recombinant albumin and serum albumin, and the serum albumin includes non-human animal (e.g., bovine) serum albumin and human serum albumin, preferably human serum albumin.

As used herein, the term "amino acid(s)" includes at least one of basic polar amino acids (such as arginine or lysine), nonpolar amino acids (such as proline), neutral polar amino acids (e.g., cysteine) and acidic polar amino acids (e.g., aspartic acid or glutamic acid), preferably arginine.

As used herein, the term "protein structure unfolding agent" refers to a substance that can unfold hydrophobic bond regions of albumin to facilitate the binding of docetaxel with albumin. All the substances with such an effect can achieve the object of the present invention. The protein structure unfolding agent includes but is not limited to one or more of mercaptoethanol, glutathione, acetylcysteine and dithiothreitol.

In a preferred embodiment, the pharmaceutical composition is a nanoparticle suspension, which comprises docetaxel in a concentration of at least 1 mg/ml, e.g., 1, 2, 3, 4, 5, 6, 7, 8, 9, 10, 20, 25, 30, 35, 40 or 50 mg/ml, and the nanoparticles therein have a particle diameter of not greater than 200 nm, e.g., 150, 100, 95, 90, 85, 80, 75, 70, 65, 60, 55 or 50 nm. The particle diameter of the nanoparticles and the concentration of docetaxel can be in any range comprised of the above values of the particle diameter or concentration.

The pharmaceutical composition of the present invention retains desired therapeutic effects, and remains physically and/or chemically stable when exposed to certain conditions, such as prolonged storage, elevated temperature or dilution for parenteral administration.

The term "physically stable" means that no substantial precipitation or sedimentation phenomenon is observed for at least about 8 hours, preferably within about 24 hours, more preferably within 48 hours, and particularly preferably within 96 hours, after reconstitution or rehydration of a lyophilized powder formulation of the pharmaceutical composition of the present invention.

The term "chemically stable" means that the chemical structure or composition of the pharmaceutical composition or active compound is stable when the pharmaceutical composition of the present invention is stored under conventional conditions. Preferably, after storage at 2-8° C. for at least 24 months, or even up to 30 months, the content percentage of 7-epi-docetaxel is ≤1.0%.

Pharmaceutical Formulation and Therapeutic Method

Another embodiment of the present invention provides a formulation comprising a therapeutically effective amount of the above docetaxel albumin nanoparticle pharmaceutical composition and a pharmaceutically acceptable carrier and/or auxiliary material. The formulation is preferably a lyophilized powder formulation.

Another embodiment of the present invention provides a use of the pharmaceutical composition or formulation of the present invention in the manufacture of a medicament for the treatment or prevention of an abnormal cell proliferative disease or disorder. The abnormal cell proliferative disease or disorder is preferably cancer, which includes prostate cancer, colon cancer, breast cancer, head and neck cancer, pancreatic cancer, lung cancer and ovarian cancer.

Another embodiment of the present invention provides a use of the pharmaceutical composition or formulation of the present invention in the manufacture of a medicament for the treatment or prevention of cancer, including prostate cancer, colon cancer, breast cancer, head and neck cancer, pancreatic cancer, lung cancer and ovarian cancer.

Another embodiment of the present invention provides a method for treating or preventing an abnormal cell proliferative disease or disorder, wherein the method comprises administering to a subject in need thereof a therapeutically effective amount of the pharmaceutical composition or formulation of the present invention. The abnormal cell proliferative disease or disorder is preferably cancer, and the cancer is preferably a specific cancer listed above.

The term "pharmaceutically acceptable carrier" refers to a diluent, auxiliary material, excipient, or vehicle with which a therapeutic is administered, and it is, within the scope of sound medical judgment, suitable for contact with the tissues of human beings and animals without excessive toxicity, irritation, allergic response, or other problem or complication, commensurate with a reasonable benefit/risk ratio.

The pharmaceutically acceptable carrier which can be employed in the formulation of the present invention includes, but is not limited to sterile liquids, such as water and oils, including those of petroleum, animal, vegetable or synthetic origin, such as peanut oil, soybean oil, mineral oil, sesame oil and the like. Water is an exemplary carrier when the formulation is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glycerol monostearate, talc, sodium chloride, dried skim milk, glycerol, propylene glycol, water, ethanol and the like. The formulation, if desired, can also contain minor amounts of wetting or emulsifying agents, or pH buffering agents. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in e.g. Remington's Pharmaceutical Sciences (1990).

The formulation can act systemically and/or locally. To this end, it can be administered through a suitable route, such as through injection, intravenous, intraarterial, subcutaneous, intraperitoneal, intramuscular, or transdermal administration, or administered via oral, buccal, nasal, transmucosal, topical, as an ophthalmic formulation, or via inhalation.

For these routes of administration, the formulation can be administered in a suitable dosage form.

Such dosage form includes, but is not limited to a spray, lotion, ointment, suspension, injectable solution, suspension injection, emulsion injection, elixir, syrup or lyophilized powder formulation.

As used herein, the term "therapeutically effective amount" refers to the pharmaceutical composition/formulation being administered which will relieve to some extent one or more of the symptoms of the disorder being treated.

Dosage regimens may be adjusted to provide the optimum desired response. For example, a single bolus may be adminstered, several divided doses may be administered over time or the dose may be proportionally reduced or increased as indicated by the exigencies of the therapeutic situation. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions.

The amount of the pharmaceutical composition/formulation of the present invention administered will be dependent on the subject being treated, the severity of the disorder or condition, the rate of administration, the disposition of the pharmaceutical composition/formulation and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases still larger doses may be employed without causing any harmful side effect, provided that such larger doses are first divided into several small doses for administration throughout the day.

The term "treating", as used herein, unless otherwise indicated, means reversing, alleviating, inhibiting the progress of, or preventing the disorder or condition to which such term applies, or one or more symptoms of such disorder or condition.

As used herein, the term "subject" includes a human or non-human animal. An exemplary human subject includes a human subject having a disease (such as one described herein) (referred to as a patient), or a normal subject. The term "non-human animal" as used herein includes all vertebrates, such as non-mammals (e.g. birds, amphibians, reptiles) and mammals, such as non-human primates, livestock and/or domesticated animals (such as sheep, dog, cat, cow, pig and the like).

Advantageous Effects of the Pharmaceutical Composition of the Present Invention

1. The amino acid(s) added significantly inhibits the formation of the 7-epi-docetaxel impurity in a docetaxel albumin nanoparticle pharmaceutical composition, enhances the stability, especially chemical stability, of the docetaxel nanoparticle pharmaceutical composition, prolongs the shelf life of the docetaxel nanoparticle pharmaceutical composition, reduces side effects or toxicity upon administration, decreases irritation to an organism, and improves clinical tolerability.

2. The method for preparing the pharmaceutical composition of the present invention is simple.

3. The present invention can be employed for the treatment of various cancers, such as prostate cancer, colon cancer, breast cancer, head and neck cancer, pancreatic cancer, lung cancer (especially non-small cell lung cancer) and ovarian cancer, etc., and thus has a broad prospect of application on the market. Moreover, the docetaxel albumin nanoparticle pharmaceutical composition of the present invention has a better therapeutic effect than that of a commercially available docetaxel injection.

EXAMPLES

The following examples are provided to further illustrate the present invention. It is necessary to be pointed out that the following examples should not be construed as limiting the protection scope of the present invention, and technical solutions obtained through certain non-substantial improvements and modifications to the technical solutions of the present invention by a skilled artisan according to the contents described above are still covered by the present invention.

The concentration of the commercially available docetaxel injection employed in the examples of the present application was 40 mg/ml. The term "docetaxel" in the examples is the docetaxel (i.e., docetaxel) compound per se.

Example 1

An organic phase was obtained by adding 100 ml of ethanol into 1500 mg of docetaxel, which was then dissolved by sonication. Human serum albumin was diluted with water for injection to formulate a 6 mg/ml solution of human serum albumin. 500 mg of glutathione was added to 1250 ml of the 6 mg/ml solution of human serum albumin, and the solution was incubated in a water bath at about 70° C. for 6 minutes to obtain an aqueous phase. The organic phase was homogeneously dispersed into the aqueous phase at high-speed shear (1,000 revolutions per minute (rpm)), and the resulting system was transferred to an equipment for concentration by ultrafiltration (PALL, 100 kD membrane). The system was concentrated by ultrafiltration to obtain a 6 mg/ml concentrate of docetaxel, wherein the docetaxel albumin nanoparticles had an average particle diameter of 103 nm (Malvern Nano-ZS90).

The above docetaxel albumin nanoparticle concentrate was divided into three portions, and arginine was added in the following ratios:

1-a. the weight ratio of arginine to docetaxel was 0.5:1;
1-b. the weight ratio of arginine to docetaxel was 1:1; and
1-c. the weight ratio of arginine to docetaxel was 20:1.

The mixed solutions containing arginine were then respectively sterilized by filtration through a 0.22 μm sterile filter head, and freeze-dried for 48 hours in a lyophilizer.

The lyophilized samples were reconstituted with physiological saline, and no precipitation was observed when the reconstituted samples were left at room temperature for 8 hours, indicating that the docetaxel albumin nanoparticle pharmaceutical composition of the present invention was physically stable. The particle diameters were measured (the average particle diameter of sample 1-a was 103 nm, the average particle diameter of sample 1-b was 102 nm, and the average particle diameter of sample 1-c was 104 nm), and the increase trends of the 7-epi-docetaxel impurity in the docetaxel albumin nanoparticle pharmaceutical compositions were determined.

Example 2

An organic phase was obtained by adding 10 ml of ethanol into 150 mg of docetaxel, which was then dissolved by sonication. Bovine serum albumin solids were dissolved with water for injection to formulate a 6 mg/ml solution of bovine serum albumin. 200 mg of glutathione and 3750 mg of proline were added to 1250 ml of the 6 mg/ml solution of bovine serum albumin, and the solution was incubated in a water bath at about 60° C. for 6 minutes to obtain an aqueous phase. The organic phase was homogeneously dispersed into the aqueous phase at high-speed shear (1,000 revolutions per minute (rpm)), and the resulting system was transferred to an equipment for concentration by ultrafiltration (PALL, 100 kD membrane). The system was concentrated by ultrafiltration to obtain a 6 mg/ml concentrate of docetaxel, wherein the final concentration of proline was 3 mg/ml, and the weight ratio of proline to docetaxel was about 0.5:1.

The docetaxel albumin nanoparticles had an average particle diameter of 113 nm (Malvern Nano-ZS90). The concentrate obtained was sterilized by filtration through a 0.22 μm sterile filter head, and freeze-dried for 48 hours in a lyophilizer. The lyophilized sample was reconstituted with physiological saline, and no precipitation was observed when the reconstituted sample was left at room temperature for 8 hours, indicating that the docetaxel albumin nanoparticle pharmaceutical composition of the present invention was physically stable.

Example 3

An organic phase was obtained by adding 10 ml of ethanol into 150 mg of docetaxel, which was then dissolved by sonication. Recombinant human serum albumin and bovine serum albumin solids (1:1 w/w) were dissolved with water for injection to formulate a 10 mg/ml solution of recombinant human serum albumin and bovine serum albumin 50 mg of glutathione was added to 450 ml of the 10 mg/ml solution of recombinant human serum albumin and bovine serum albumin, and the solution was incubated in a water bath at 60° C. for 6 minutes to obtain an aqueous phase. The organic phase was homogeneously dispersed into the aqueous phase at high-speed shear (1,000 revolutions per minute (rpm)), and the resulting system was transferred to an equipment for concentration by ultrafiltration (PALL, 100 kD membrane). The system was concentrated by ultrafiltration to obtain a 6 mg/ml concentrate of docetaxel. Proline was then added to the concentrate, such that the weight ratio of proline to docetaxel was 1:1. The docetaxel albumin nanoparticles had an average particle diameter of 110 nm (Malvern Nano-ZS90). The concentrate obtained was sterilized by filtration through a 0.22 μm sterile filter head, and freeze-dried for 48 hours in a lyophilizer. The lyophilized sample was reconstituted with physiological saline, and no precipitation was observed when the reconstituted sample was left at room temperature for 8 hours, indicating that the docetaxel albumin nanoparticle pharmaceutical composition of the present invention was physically stable.

Example 4

The product was prepared according to the process of Example 1, except ethanol was replaced by tert-butyl alcohol, glutathione was replaced by acetylcysteine, and arginine was replaced by lysine (the weight ration of lysine to docetaxel was 1, i.e., was 1:1). The particle diameter of the docetaxel albumin nanoparticles was 124 nm.

Example 5

The product was prepared according to the process of Example 1, except ethanol was replaced by a mixture of acetone and tert-butyl alcohol (1:1 v/v), glutathione was replaced by mercaptoethanol, and arginine was replaced by cysteine (the weight ration of cysteine to docetaxel was 1, i.e., was 1:1). The particle diameter of the docetaxel albumin nanoparticles was 132 nm.

Example 6

The product was prepared according to the process of Example 1, except glutathione was replaced by a mixture of dithiothreitol and mercaptoethanol (1:1 w/w), arginine was replaced by a mixture of arginine and proline (the weight ration of arginine and proline was 1:1, and the weight ration of the mixture of amino acids to docetaxel was 1, i.e., was 1:1), and the concentration of docetaxel after concentration was 1 mg/ml. The particle diameter of the docetaxel albumin nanoparticles was 200 nm.

Example 7

The product was prepared according to the process of Example 1, except no glutathione was added, and arginine was replaced by glutamic acid (the weight ration of glutamic acid to docetaxel was 1:1). The particle diameter of the docetaxel albumin nanoparticles was 183 nm.

Example 8

The product was prepared according to the process of Example 2, except no glutathione was added, and proline was replaced by glutamic acid (the weight ratio of glutamic acid to docetaxel was 1:1). The particle diameter of the docetaxel albumin nanoparticles was 196 nm.

Comparative Example 1

An organic phase was obtained by adding 150 mg of docetaxel into a 50 ml vial, followed by addition of 10 ml of ethanol, and docetaxel was dissolved by sonication. A concentrated solution (200 mg/ml) of human serum albumin was diluted with water for injection to formulate a 6 mg/ml solution. 50 mg of glutathione was added to 125 ml of the 6 solution of human serum albumin, and the solution was incubated in a water bath at 80° C. for 6 minutes. The organic phase was then homogeneously dispersed into the aqueous phase at high-speed shear (1,000 revolutions per minute (rpm)), and the resulting system was transferred to an equipment for concentration by ultrafiltration (PALL, 100 kD membrane). The system was concentrated by ultrafiltration to obtain a 10 concentrate of docetaxel. Tartaric acid (salt) was then added, such that the final solution had a pH of 7.0, and contained docetaxel in a concentration of 6 mg/ml, and tartaric acid (salt) in a concentration of 100 mM (reference: the preferred ratios in CN103054798A). The sample of the final solution was sterilized by filtration through a 0.22 μm sterile filter head, and freeze-dried for 48 hours in a lyophilizer.

Comparative Example 2

The product was prepared according to the process of Comparative Example 1, except tartaric acid was replaced by citric acid, and the final concentration was 100 mM (reference: the preferred ratios in CN103054798A).

Comparative Example 3

The product was prepared according to the process of Comparative Example 1, except tartaric acid was replaced by sodium citrate, and the final concentration was 100 mM (reference: the preferred ratios in CN103054798A).

Comparative Example 4

The product was prepared according to the process of Example 1, except no amino acid was added.

Experimental Example 1: Storage Stability

After being left at 2-8° C. for various periods (see Table 1), the products of Examples 1 to 8 and Comparative Examples 1 to 4 were added with appropriate amounts of a 0.9% sodium chloride solution. After the products were uniformly dispersed, about 300 μl of each of the samples was accurately weighed, placed in a 2 ml centrifuge tube, and 600 μl of acetonitrile was added accurately. After being vortexed for 30 seconds, the samples were subjected to solid phase extraction, and the resulting extraction solutions were filtered, so as to facilitate the detection of the content of 7-epi-docetaxel.

The contents in percentage of 7-epi-docetaxel were determined by HPLC, and the chromatographic conditions were as follows: column: Spherisorb RP18 4.6×250 nm, particle diameter: 5 μm; mobile phase: solution A=acetonitrile:water (2:3, V/V), and solution B=acetonitrile; elution was carried out with solution A for the first 70 minutes, and then with 10% solution A and 90% solution B for 20 minutes; flow rate: 1 ml/min; detection wavelength: 227 nm; and injection volume: 20 μl.

The increments (represented by peak area percentages in the HPLC chromatograms) of 7-epi-docetaxel in the docetaxel albumin nanoparticle pharmaceutical compositions after storage at 2-8° C. is shown in Table 1.

TABLE 1

The increase of the content of 7-epi-docetaxel (increment % = the peak area % after N months − the peak area % on day 0)

| Group | increment % of 7-epi-docetaxel | | | | |
|---|---|---|---|---|---|
| | 3 months | 6 months | 12 months | 24 months | 30 months |
| Comparative Example 1 | 0.45% | 0.81% | 1.54% | 2.65% | N/A |
| Comparative Example 2 | 0.44% | 0.86% | 1.39% | 2.56% | N/A |
| Comparative Example 3 | 0.43% | 0.85% | 1.36% | 2.47% | N/A |
| Comparative Example 4 | 0.45% | 0.87% | 1.49% | 2.79% | N/A |
| Example 1-a | 0.02% | 0.14% | 0.37% | 0.58% | 0.74% |
| Example 1-b | 0.01% | 0.11% | 0.34% | 0.49% | 0.61% |
| Example 1-c | 0.04% | 0.07% | 0.30% | 0.41% | 0.54% |
| Example 2 | 0.02% | 0.15% | 0.37% | 0.70% | N/A |
| Example 3 | 0.04% | 0.16% | 0.32% | 0.63% | N/A |
| Example 4 | 0% | 0.19% | 0.37% | 0.66% | N/A |
| Example 5 | 0.07% | 0.26% | 0.43% | 0.64% | N/A |
| Example 6 | 0.03% | 0.14% | 0.39% | 0.53% | N/A |
| Example 7 | 0.03% | 0.2% | 0.43% | 0.63% | N/A |
| Example 8 | 0.7% | 0.24% | 0.46% | 0.79% | N/A |

Note 1:
The acceptable limit for the stability of the docetaxel albumin nanoparticle composition (i.e., the highest content of 7-epi-docetaxel) is normally "a content percentage of 7-epi-docetaxel ≤1.0%";
Note 2:
N/A means no detection was performed.

The experimental results showed that the addition of arginine, lysine, proline, cysteine, glutamic acid or a combination thereof to the docetaxel albumin nanoparticle composition as prepared in the examples of the present application can effectively inhibit the degradation of docetaxel, and reduce the increase of the content of the epimer, 7-epi-docetaxel. It was also shown in Table 1 that the addition of an organic acid (or a salt thereof) with pKa of 2.5 to 4.5 cannot inhibit the increase of the content of the epimer, 7-epi-docetaxel.

In the above tests, the products of Examples 1-a, 1-b and 1-c of the present invention, wherein arginine was employed as an impurity inhibitor, achieved the best effects: it can be stored at 2-8° C. for at least 24 months, or even up to 30 months.

Experimental Example 2: Storage Stability

Docetaxel albumin compositions comprising no arginine or comprising arginine and docetaxel in a weight ratio of 80:1 were prepared, and content percentages of 7-epi-docetaxel were determined according to Experimental Example 1. The peak area percentages in the HPLC chromatograms over time are shown in Table 2. As can be seen from Table 2, when the ratio of arginine to docetaxel was 80, the increase of the content of 7-epi-docetaxel in the composition was inhibited during 30 months storage at 2-8° C.

TABLE 2

The increase of the content of 7-epi-docetaxel (increment % = the peak area % after N months – the peak area % on day 0)

| Ratio of arginine to docetaxel | increment % of 7-epi-docetaxel | | | | |
|---|---|---|---|---|---|
| | 3 months | 6 months | 12 months | 24 months | 30 months |
| 0 (0:1) | 0.47% | 0.87% | 1.56% | 2.76% | 4.23% |
| 80 (80:1) | 0.01% | 0.04% | 0.22% | 0.38% | 0.49% |

As can be seen from Experimental Examples 1 and 2, the docetaxel albumin nanoparticles prepared in the examples of the present application have good physical and chemical stability, are not liable to degradation, have less impurity after conventional storage and transportation, and certainly would have less toxic and side effects caused by the impurity.

Experimental Example 3: Antitumor Activity

The use of the compositions prepared in the present application for the treatment of cancer was demonstrated by a pharmacological efficacy verification test on a tumor model of BALB/c nude mice with a subcutaneous xenograft of human non-small cell lung cancer cell A549.

Thirty qualified BALB/c animals bearing a tumor of A549 cells were selected, and randomly divided into three groups (10 mice per group), which were a group administered with physiological saline (blank control), a group administered with a commercially available docetaxel injection (20 mg/kg) and a group administered with the docetaxel albumin nanoparticle (20 mg/kg) according to Example 1-c of the present invention, respectively. The administration was performed through intravenous injection via tail vein for 4 weeks. During the administration, general clinical symptoms of the animals were observed twice a day, the body weight and tumor diameter were measured twice a week, and the tumor weight was measured at the end. The tumor size was plotted versus time, so as to obtain a curve for the evaluation of pharmacological efficacy.

The pharmacological efficacy results are shown in FIG. 1. As shown in FIG. 1, the docetaxel albumin nanoparticle pharmaceutical composition according to Example 1-c of the present invention achieved a significant inhibitory effect on tumor growth on the tumor model of BALB/c nude mice with a subcutaneous xenograft of non-small cell lung cancer cell A549, and the effect of the docetaxel albumin nanoparticle composition according to Example 1-c of the present invention was better that that of the commercially available docetaxel injection.

Experimental Example 4: Antitumor Activity

The use of the compositions prepared in the present application for the treatment of cancer was demonstrated by a pharmacological efficacy verification test with the docetaxel albumin nanoparticle pharmaceutical composition of Example 7 of the present invention on a tumor model of BALB/c nude mice with a subcutaneous xenograft of human non-small cell lung cancer cell A549.

Thirty qualified BALB/c animals bearing a tumor of A549 cells were selected, and randomly divided into three groups (10 mice per group), which were a group administered with physiological saline (blank control), a group administered with a commercially available docetaxel injection (16 mg/kg) and a group administered with the docetaxel albumin nanoparticle (13.6 mg/kg) according to Example 7 of the present invention, respectively. The administration was performed through intravenous injection via tail vein for 4 weeks. During the administration, general clinical symptoms of the animals were observed twice a day, and the body weight and tumor diameter were measured twice a week.

The pharmacological efficacy results are shown in Table 3. The docetaxel albumin nanoparticle pharmaceutical composition according to Example 7 of the present invention achieved a significant inhibitory effect on tumor growth on the tumor model of BALB/c nude mice with a subcutaneous xenograft of non-small cell lung cancer cell A549. After administered for 21 days, the inhibition rate of tumor achieved by the docetaxel albumin nanoparticle composition of Example 7 (administered dose: 13.6 mg/kg) was 112%, while the inhibition rate of tumor achieved by the commercially available docetaxel injection (administered dose: 16 mg/kg) was 99%. It can be seen that the docetaxel albumin nanoparticle of the present invention achieved a high inhibition rate of tumor at a low dose, had a therapeutic effect significantly better than that of the commercially available docetaxel injection, and had an excellent therapeutic effect on human non-small cell lung cancer.

TABLE 3

The therapeutic effect on nude mice with a subcutaneous xenograft of human non-small cell lung cancer cell A549

| Group | Administration dose (mg/kg) | Tumor volume on day 0 (mm³) | Tumor volume on day 21 (mm³) | Inhibition rate of tumor (%) |
|---|---|---|---|---|
| Physiological saline | — | 149.2 | 1218.9 | — |
| Composition of Example 7 | 13.6 | 152.2 | 133.7 | 112 |
| Commercially available docetaxel injection | 16 | 141.2 | 151.5 | 99 |

Experimental Example 5: Antitumor Activity

The use of the compositions prepared in the present application for the treatment of cancer was demonstrated by a pharmacological efficacy verification test with the docetaxel albumin nanoparticle pharmaceutical composition of Example 7 of the present invention on a tumor model of BALB/c nude mice with a subcutaneous xenograft of human ovarian cancer cell SK-OV-3.

Fifty qualified BALB/c animals bearing a tumor of SK-OV-3 cells were selected, and randomly divided into five groups (10 mice per group), which were a group administered with physiological saline (blank control), group 1 administered with a commercially available docetaxel injection (9.9 mg/kg), group 2 administered with a commercially available docetaxel injection (16 mg/kg), group 1 administered with the docetaxel albumin nanoparticle (8.5 mg/kg)

according to Example 7 of the present invention, and group 2 administered with the docetaxel albumin nanoparticle (13.6 mg/kg) according to Example 7 of the present invention, respectively. The administration was performed through intravenous injection via tail vein for 4 weeks. During the administration, general clinical symptoms of the animals were observed twice a day, and the body weight and tumor diameter were measured twice a week.

The pharmacological efficacy results are shown in Table 4. The docetaxel albumin nanoparticle pharmaceutical composition according to Example 7 of the present invention achieved a significant inhibitory effect on tumor growth on the tumor model of BALB/c nude mice with a subcutaneous xenograft of ovarian cancer cell SK-OV-3. After administered for 18 days, the inhibition rate of tumor achieved by the docetaxel albumin nanoparticle composition of Example 7 (administered dose: 8.5 mg/kg) was 65%, while the inhibition rate of tumor achieved by the commercially available docetaxel injection (administered dose: 9.9 mg/kg) was 55%. When the pharmaceutical composition of Example 7 of the present invention was administered at a dose of 13.6 mg/kg and the commercially available docetaxel injection was administered at a dose of 16 mg/kg, the tumor inhibition rate were both 87% after administration for 18 days. According to the above experimental results, compared with the commercially available docetaxel injection, the composition of the present invention achieved a better or equivalent inhibitory effect on tumor at a lower dose, which demonstrated that the docetaxel albumin nanoparticle of the present invention had an excellent therapeutic effect on human ovarian cancer.

TABLE 4

The therapeutic effect on nude mice with a subcutaneous xenograft of human ovarian cancer cell SK-OV-3

| Group | Administration dose (mg/kg) | Tumor volume on day 0 (mm³) | Tumor volume on day 18 (mm³) | Inhibition rate of tumor (%) |
| --- | --- | --- | --- | --- |
| Physiological saline | — | 146.7 | 1876.3 | — |
| Composition of Example 7 (group 1) | 8.5 | 145.0 | 758.1 | 65 |
| Commercially available docetaxel injection (group 1) | 9.9 | 144.0 | 930.3 | 55 |
| Composition of Example 7 (group 2) | 13.6 | 145.3 | 361.8 | 87 |
| Commercially available docetaxel injection (group 2) | 16 | 145.8 | 373.8 | 87 |

Although the present invention has been further described through the above specific examples, it should be understood that it is not limited thereby. The present invention encompasses general aspects of the above disclosures, and a person skilled in the art is able to make various modifications or change various details of the present invention without departing from the spirit and scope of the present invention. Thus, the present description is presented for purposes of illustration only and not by way of limitation.

The invention claimed is:

1. A storage stable docetaxel albumin nanoparticle pharmaceutical composition comprising:
   docetaxel,
   albumin, and
   amino acid(s),
   wherein the weight ratio of albumin to docetaxel is from 50:1 to 1:1;
   wherein the weight ratio of the amino acid(s) to docetaxel is from 1:1 to 20:1;
   wherein the amino acid(s) is selected from the group consisting of arginine, lysine, proline, cysteine, glutamic acid and mixtures thereof; and
   wherein the amino acid(s) inhibits the formation of the 7-epi-docetaxel impurity of docetaxel in the pharmaceutical composition thereby forming a storage stable pharmaceutical composition.

2. The pharmaceutical composition according to claim 1, wherein the amino acid(s) is the only stabilizer in the pharmaceutical composition.

3. The pharmaceutical composition according to claim 1, wherein the pharmaceutical composition optionally comprises a protein structure unfolding agent, which includes one or more of mercaptoethanol, glutathione, and acetylcysteine, and wherein the weight ratio of albumin to the protein structure unfolding agent is from 50:1 to >0:1.

4. The pharmaceutical composition according to claim 1, wherein the pharmaceutical composition is a nanoparticle suspension, which comprises docetaxel in a concentration of at least 1 mg/ml, and wherein the nanoparticles therein have a particle diameter of not greater than 200 nm.

5. The pharmaceutical composition according to claim 1, wherein the albumin includes one or more of recombinant albumin and serum albumin.

6. A method for preparing the pharmaceutical composition according to claim 1, wherein the method comprises the following steps:
   1) dissolving docetaxel in an organic solvent preferably selected from one or more of ethanol, tert-butyl alcohol, and acetone, to obtain an organic phase;
   2) using an aqueous solution containing amino acid(s) to dissolve albumin or to dilute a solution of albumin, so as to obtain a solution of albumin and amino acid(s);
   3) subjecting the solution of albumin and amino acid(s) obtained in step 2) to an incubation reaction;
   4) adding the organic phase obtained in step 1) to the solution obtained after the incubation reaction in step 3) under shear, to obtain a dilute solution of docetaxel albumin nanoparticles; and
   5) concentrating the solution obtained in step 4) by ultrafiltration, to obtain a docetaxel albumin nanoparticle pharmaceutical composition with enhanced stability;
   wherein the enhanced stability is achieved by the amino acid(s) through inhibiting the formation of the 7-epi-docetaxel impurity in the docetaxel albumin nanoparticle pharmaceutical composition;
   wherein the weight ratio of albumin to docetaxel is not greater than 50, i.e., is from 50:1 to >0:1, preferably is from 50:1 to 1:1, and more preferably is from 20:1 to 1:1;
   wherein the weight ratio of the amino acid(s) to docetaxel is no less than 0.5, i.e., is ≥0.5:1, preferably is from 0.5:1 to 80:1, more preferably is no less than 1, i.e., is ≥1:1, and preferably is from 1:1 to 20:1; and
   wherein the amino acid(s) preferably includes at least one of arginine, lysine, proline, cysteine, and glutamic acid, and preferably is arginine.

7. The method according to claim 6, wherein step 3) further comprises adding a protein structure unfolding agent to the solution of albumin and amino acid(s) obtained in step 2) before performing the incubation reaction; wherein the protein structure unfolding agent includes one or more of mercaptoethanol, glutathione, acetylcysteine, and dithiothreitol, and wherein the weight ratio of albumin to the protein structure unfolding agent is not greater than 100:1, i.e., is from 100:1 to >0:1, and preferably is from 50:1 to >0:1.

8. The method according to claim 6, wherein alternatively, steps 2) and 3) are performed as follows: using water for injection to dissolve albumin or to dilute a solution of albumin, so as to obtain a solution of albumin, and then adding amino acid(s) before subjecting the solution to an incubation reaction.

9. The method according to claim 6, wherein alternatively, steps 2) and 3) are performed as follows: using water for injection to dissolve albumin or to dilute a solution of albumin, so as to obtain a solution of albumin; adding amino acid(s) and a protein structure unfolding agent to the solution, and performing an incubation reaction; wherein the protein structure unfolding agent includes one or more of mercaptoethanol, glutathione, acetylcysteine, and dithiothreitol; and wherein the weight ratio of albumin to the protein structure unfolding agent is not greater than 100:1, i.e., is from 100:1 to >0:1, and preferably is from 50:1 to >0:1.

10. The method according to claim 6, wherein alternatively, steps 2) and 3) are performed as follows: using water for injection to dissolve albumin or to dilute a solution of albumin, so as to obtain a solution of albumin, and subjecting the solution of albumin to an incubation reaction; and step 5) is performed as follows: concentrating the solution by ultrafiltration before adding amino acid(s) to the concentrate, to obtain a docetaxel albumin nanoparticle pharmaceutical composition with enhanced stability.

11. The method according to claim 6, wherein alternatively, steps 2) and 3) are performed as follows: using water for injection to dissolve albumin or to dilute a solution of albumin, so as to obtain a solution of albumin, adding a protein structure unfolding agent to the solution, and performing an incubation reaction; and wherein step 5) is performed as follows: concentrating the solution by ultrafiltration before adding amino acid(s) to the concentrate, to obtain a docetaxel albumin nanoparticle pharmaceutical composition with enhanced stability; wherein the protein structure unfolding agent includes one or more of mercaptoethanol, glutathione, acetylcysteine, and dithiothreitol, and wherein the weight ratio of albumin to the protein structure unfolding agent is not greater than 100:1, i.e., is from 100:1 to >0:1, and preferably is from 50:1 to >0:1.

12. A formulation comprising the docetaxel albumin nanoparticle pharmaceutical composition according to claim 1, wherein the formulation further comprises a pharmaceutically acceptable carrier and/or auxiliary material; and wherein the formulation is an injectable solution, injectable suspension, injectable emulsion, or lyophilized powder formulation.

13. A formulation comprising the docetaxel albumin nanoparticle pharmaceutical composition prepared according to the method of claim 10, wherein the formulation further comprises a pharmaceutically acceptable carrier and/or auxiliary material; and wherein the formulation is an injectable solution, injectable suspension, injectable emulsion, or lyophilized powder formulation, and preferably is a lyophilized powder formulation.

14. A method for the treatment or prevention of an abnormal cell proliferative disease or disorder, wherein the method comprises administering the pharmaceutical composition according to claim 1 to a subject in need thereof.

15. A method for the treatment or prevention of cancer, wherein the cancer includes prostate cancer, gastric cancer, colon cancer, breast cancer, head and neck cancer, pancreatic cancer, lung cancer and ovarian cancer, wherein the method comprises administering the pharmaceutical composition according to claim 1 to a subject in need thereof.

16. A method for inhibiting the formation of the 7-epi-docetaxel impurity in a docetaxel albumin nanoparticle pharmaceutical composition, wherein the method comprises adding amino acid(s) to the pharmaceutical composition; the amino acid(s) preferably includes at least one of arginine, lysine, proline, cysteine, and glutamic acid, and more preferably the amino acid(s) is arginine.

17. The method according to claim 16, wherein the pharmaceutical composition comprises:
docetaxel,
albumin, and
amino acid(s),
wherein the weight ratio of albumin to docetaxel is not greater than 50, i.e., is from 50:1 to >0:1, preferably is from 50:1 to 1:1, and more preferably is from 20:1 to 1:1;
wherein the weight ratio of the amino acid(s) to docetaxel is no less than 0.5, i.e., is ≥0.5:1, preferably is from 0.5:1 to 80:1, more preferably is no less than 1, i.e., is ≥1:1, and preferably is from 1:1 to 20:1; and
wherein the amino acid(s) includes at least one of arginine, lysine, proline, cysteine, and glutamic acid, and preferably is arginine.

18. A method for improving the stability of a docetaxel albumin nanoparticle pharmaceutical composition, wherein the method comprises adding amino acid(s) to the docetaxel albumin nanoparticle pharmaceutical composition, so as to inhibit the formation of the 7-epi-docetaxel impurity therein, thereby improving the stability; the amino acid(s) preferably includes at least one of arginine, lysine, proline, cysteine, and glutamic acid, and more preferably the amino acid(s) is arginine.

19. The method according to claim 18, wherein the pharmaceutical composition comprises:
docetaxel,
albumin, and
amino acid(s),
wherein the weight ratio of albumin to docetaxel is not greater than 50, i.e., is from 50:1 to >0:1, preferably is from 50:1 to 1:1, and more preferably is from 20:1 to 1:1;
wherein the weight ratio of the amino acid(s) to docetaxel is no less than 0.5, i.e., is ≥0.5:1, preferably is from 0.5:1 to 80:1, more preferably is no less than 1, i.e., is ≥1:1, and preferably is from 1:1 to 20:1; and
wherein the amino acid(s) includes at least one of arginine, lysine, proline, cysteine, and glutamic acid, and preferably is arginine.

20. The pharmaceutical composition according to claim 1, wherein the weight ratio of albumin to docetaxel is from 20:1 to 1:1.

21. The pharmaceutical composition according to claim 1, wherein the amino acid is arginine.

22. The pharmaceutical composition according to claim 1, wherein the albumin is human serum albumin.

* * * * *